United States Patent [19]

Hills

[11] Patent Number: 5,403,592
[45] Date of Patent: Apr. 4, 1995

[54] LUBRICANT COMPOSITION FOR RHEUMATISM

[75] Inventor: Brian A. Hills, New South Wales, Australia

[73] Assignee: MacNaught Pty Limited, Turrella, Australia

[21] Appl. No.: 466,257

[22] PCT Filed: Aug. 25, 1987

[86] PCT No.: PCT/AU88/00322

§ 371 Date: Jun. 18, 1990

§ 102(e) Date: Jun. 18, 1990

[30] Foreign Application Priority Data

Aug. 25, 1987 [AU] Australia ................. PI3944

[51] Int. Cl.$^6$ ............ A61K 37/22; A61K 31/685
[52] U.S. Cl. .................... 424/450; 514/78; 514/825
[58] Field of Search ........... 514/78, 825; 424/450

[56] References Cited

U.S. PATENT DOCUMENTS

| | | | |
|---|---|---|---|
| 4,427,649 | 1/1984 | Dingle et al. | 514/174 |
| 4,937,254 | 6/1990 | Sheffield et al. | 514/420 |
| 4,946,683 | 8/1990 | Forssen | 424/422 |

*Primary Examiner*—Raymond Henley, III
*Assistant Examiner*—K. Weddington
*Attorney, Agent, or Firm*—McAulay Fisher Nissen Goldberg & Kiel

[57] ABSTRACT

A composition comprised of at least one surface active phospholipid, hyaluronic acid or a water soluble salt thereof in saline solution for use as a lubricant, in particular, for physiological use such as the lubrication of joints. The composition can be used to reduce the coefficient of kinetic friction between surfaces in contact with each other, particularly load-bearing surfaces.

16 Claims, No Drawings

LUBRICANT COMPOSITION FOR RHEUMATISM

This invention relates to lubricant compositions and in particular, compositions adapted for physiological use such as the lubrication of joints.

In man and other animals it is known that synovial fluid acts to effectively lubricate the surfaces of bones that are in frictional contact to form joints. Moreover, the synovial fluid is able to provide effective lubrication in joints such as the human knee, where the normal applied load is about 3 kg. cm$^{-2}$.

Due to the widespread and debilitating effects of osteoarthritis and other rheumatic diseases, considerable attention has been paid to developing a lubricant effective for irrigating arthritic joints. Such a lubricant would help to keep the joint mobile and reduce mechanical stress causing pain during movement. Additionally, the lubricant would desirably:

1. reduce wear of the articular surfaces;
2. facilitate release of surfaces in initiating motion; and
3. render the surfaces hydrophobic and, hence, less permeable to fluid whose expression from the joint can contribute to the hydration of cartilage which is a common finding in arthritis.

It is to be noted that a lubricant of the aforementioned type would also be effective in other tissues where surfaces are in sliding contact such as the heart, lungs and in muscle fibres.

Accordingly, attention has been directed towards identifying an "active ingredient" present in synovial fluid that is able to effectively lubricate joints.

It has been recognised that one of the major components of synovial fluid is hyaluronic acid, which has a co-efficient of kinetic friction below 0.02. However, its lubricating ability fails when it is loaded above about 0.5–1 kg. cm$^{-2}$. It would therefore fail well below the normal load of about 3 kg. cm$^{-2}$ borne by the knee joints of man.

The finding of the failure of hyaluronic acid to effectively lubricate under such loads has raised the question as to the nature of the surface active ingredient which would normally be present in a joint rendering the articular surfaces of the joint hydrophobic.

It has further been observed that good lubrication of joints is achieved when synovial fluid is replaced by saline thus suggesting that the active ingredient is adsorbed onto the articular surfaces.

In studying the sliding of the pleural surfaces in the lung, the present inventor found phospholipids in pleural fluid and has shown that phospholipids can lubricate well as a layer adsorbed to such surfaces as glass or quartz when deposited onto those surfaces from solution in chloroform. Further, studies showed that these layers had high-load-bearing properties and that the same phospholipids are present in many other fluids adjacent to sliding tissue surfaces, for example, the pericardium, numerous visceral surfaces and the joints. Moreover, they are present in a surface active state which would be needed for them to be adsorbed to the sliding surfaces in vivo.

The results of those experiments have shown that layers of certain phospholipids, especially the disaturated phosphatidylcholines (lecithins), can give coefficients of kinetic friction of less than 0.01 and sometimes as low as 0.002 when deposited by evaporation from solution in chloroform. Moreover, such low values for coefficient of kinetic friction may be obtained for loads as high as 13 kg. cm$^{-2}$. These findings may explain why joint lubrication has the characteristics of boundary lubrication and yet coefficients of friction of a magnitude generally associated with hydrodynamic lubrication.

The present inventor has found that a composition having a suitably low coefficient of kinetic friction of the order of 0.003–0.010 may be prepared by the ultrasonication of surface active phospholipid in saline to produce a suspension of liposomes. It has further been found that lower coefficients of kinetic friction may be obtained when a surface active phospholipid is suspended in hyaluronia acid. Such compositions give suitably low coefficients of kinetic friction at relatively high loads.

The present invention relates to a lubricant composition comprised of at least one surface active phospholipid, hyaluronic acid or a water soluble salt thereof in saline solution. The saline solution preferably is 0.9% NaCl solution, optionally phosphate-buffed 0.9% NaCl solution. The lubricant composition may optionally contain pharmaceutically acceptable excipients and/or additives.

The introduction of a lubicant composition, in accordance with the present invention, having a relatively high concentration of phospholipid in solution, said phospholipid being taken from either synovial fluid or from another site where lubrication of tissue takes place in the body, into the joint of an animal or a human leads to improved lubrication of the articular surfaces of said joint. A higher degree of improved lubrication is obtained when the concentration of the phospholipid in the lubricant composition exceeds the normal concentration of phospholipid found in synovial fluid. The adsorption of phospholipid onto the articular surfaces of a aforesaid low coefficients of kinetic friction.

The increase in phospholipid concentration at a particular site, resulting from the introduction of a lubricant composition at said site, can also serve as a releasing agent, that is, prevent the sticking of a joint after standing when fluids can be "squeezed out". Thus, the surface active phospholipid present in the lubricant composition can be used as a release agent when said composition is used in conjunction with the synovial fluid of a joint or of those sites of the body where surfaces are in contact. Such a use would result in increased mobility and decreased pain, if present, at the particular site. In some cases where the composition is used as a release agent the force of adhesion by a protein glue can be reduced by 90 to 99%.

The improved effects obtained through the administration of a lubricant composition can be maintained or readily re-established by irrigating the joint or site previously affected by a lubricant composition at regular intervals as required.

Thus, the present invention also relates to a method of use of a lubricant composition wherein said lubricant composition is introduced into the synovial fluid of a joint of an animal or a human resulting in the increased adsorption of phospholipids onto the articular surfaces of said joint such that the coefficient of kinetic friction between the articular surfaces and the synovial fluid and between the articular surfaces themselves is reduces.

In addition, the present invention relates to the use of a lubricant composition as a releasing agent when said lubricant composition is used in conjunction with the synovial fluid of a particular joint or at a particular site in a body where surfaces are in contact.

The present invention also provides a method for the treatment of osteoarthritis and related diseases of the joints of animals comprising administering to a disease affected joint an effective amount of a lubricant composition. A preferred method of administering the invention lubricant composition to a joint is by injection. Accordingly, the hyaluronic acid will need to be of a purity so as not to invoke an inflammatory response when injected into the joint.

As referred to in this specification and claims, surface active phospholipids refers to any one or more of the phospholipids selected from the sphingolipids and phosphoglycerides. Surface active phospholipids which can be used in accordance with the present invention include phospholipids which may be naturally or artificially synthesized. Surface active phospholipids are preferably selected from the group comprised of phosphatidylcholine, phosphatidylethanolamine, phosphatidylserine, phosphatidylglycerol, phosphatidylinositol, sphingomyelin and derivatives thereof. Additionally, mixtures of two or more of the aforementioned phospholipids may be used.

In a particularly preferred embodiment the surface active phospholipid is alpha-dipalmitoyl phosphatidylcholine (alpha-DPPC), most preferably, the racemic (DL) mixture of alpha-DPPC. The racemic mixture provides enhanced effectiveness as a result of the phospholipases found in vivo eventually break down the L form and thereby leaving the D form to continue to lubricate the surface. This would have the potential advantage of extending the period between irrigation of arthritic joints. Preferably, the DL alpha-DPPC is synthetically derived and therefore its use would circumvent the risk of cross infection inherent in the use of L alpha DPPC derived from biological sources. The concentration of surface active phospholipids in the lubricant composition is between 1 to 200 mg. ml$^{-1}$.

The compositions of the present invention, being aqueous solutions, are readily usable and physiologically suitable for application in the lubrication of joints. In such cases it would appear that hyaluronic acid and phospholipids present in the joint act synergistically. This may be the result of either hyaluronic acid facilitating the lubrication of the phospholipids or the phospholipids promoting the load bearing of the hyaluronic acid.

The hyaluronic acid of a lubricant composition may be present as a water soluble salt, such as the sodium or potassium salt, or mixtures thereof. Further, a multivalent metal cation may be substituted for the sodium or potassium ion of the salt whereby hydrophobicity can be increased. Suitable cations for this purpose include $Ca^{2+}$, $Al^{3+}$ and $Au^{4+}$. Typically, a lubricant composition would contain from 1 to 10 mg. ml$^{-1}$ of hyaluronic acid, whilst in those compositions which include multivalent cations, the multivalent cation will be present in a concentration of 1 to 10 mM.

In preferred forms, lubricant compositions in accordance with the invention have coeffecients of kinetic friction of the order of 0,003 to 0,008 at loads as high as 13 kg. cm$^{-2}$. It will therefore be realised that the lubricant composition would be capable of providing sufficient lubrication even in such high load bearing joints as the human knee.

From the foregoing, it is evident that the present invention is able to provide effective lubricant compositions, particularly for use in physiological circumstances such as the lubrication of joints.

Some other physiological uses for the compositions of the present invention include use in the prevention of adhesion formation following abdominal surgery, particularly where make-up doses are given intraperitoneally, and as lubricants elsewhere in the body, for example, for "pleural rub", "pericardial rub" and inter-fibre relaxation in muscular tissue. Note that this latter use has implications for the treatment of fibrocytis.

An additional use is the reduction of membrane permeability such as the chorioamnionic sac. Such membrane surfaces are also rendered hydrophobic. This property is also potentially useful in the treatment of arthritic joints since an impermeable hydrophobic articular surface is desirable even if joint lubrication is hydrodynamic.

It will be recognised by persons skilled in the art that, in respect of the invention as described, numerous variations and modifications are possible without departing from the spirit or scope thereof.

I claim:

1. A lubricant composition for parenteral administration to a joint, consisting essentially of
   (a) at least one surface active phospholipid selected from the group consisting of sphingolipids and phosphoglycerides,
   (b) at least one member selected from the group consisting of hyaluronic acid and its water soluble salts, and saline solution.

2. A composition according to claim 1, wherein the concentration of the surface active phospholipid is between 1 to 200 mg ml$^{-1}$.

3. A composition according to claim 1 wherein the concentration of hyaluronic acid is from 1 to 10 mg ml$^{-1}$.

4. A composition according to claim 1, wherein the hyaluronic acid salt is selected from sodium, potassium, calcium, aluminium or gold salts of hyaluronic acid.

5. A composition according to claim 1, wherein the concentration of the hyaluronic acid or salt thereof containing a monovalent cation is from 1 to 10 mg. ml$^{-1}$.

6. A composition according to claim 1, wherein the concentration of the hyaluronic salt containing a multivalent cation is from 1 to 10 mM.

7. A composition according to claim 1, wherein said phospholipid is selected from the group consisting of phosphatidylcholine and derivatives thereof.

8. A composition according to claim 1, wherein the phospholipid is alpha-dipalmitoyl phosphatidylcholine.

9. A composition according to claim 1, wherein the phospholipid is a racemic mixture of D-alpha-dipalmitoyl phosphatidylcholine and L-alpha-dipalmitoyl phosphatidylcholine.

10. A composition of claim 1 wherein the surface active phospholipid is suspended in the hyaluronic acid or salts thereof.

11. A composition of claim 1 when introduce into a joint of an animal or a human.

12. A composition of claim 1 when used to reduce the coefficient of kinetic friction imparted to the boundary surfaces of a join of an animal or human upon articulation to a value of between 0.003 to 0.05.

13. A composition according to claim 12, wherein the reduced coefficient of kinetic friction occurs at loading values on said surfaces up to 20 kg. cm$^{-2}$.

14. A method for the treatment of arthritic joints comprising administering an anti-arthritic effective amount of a composition consisting essentially of
   (a) at least one surface active phospholipid selected from the group consisting of sphingolipids and phosphoglycerides,
   (b) at least one member selected from the group consisting of hyaluronic acid and its water soluble salts, and
   (c) saline solution.

15. A method for the treatment of osteoarthritis comprising administering an anti-osteoarthritis effective amount of a composition consisting essentially of
   (a) at least one surface active phospholipid selected from the group consisting of sphingolipids and phosphoglycerides,
   (b) at least one member selected from the group consisting of hyaluronic acid and its water soluble salts, and
   (c) saline solution.

16. A method for the treatment of rheumatic disease comprising administering an anti-rheumatic disease effective amount of a composition consisting essentially of
   (a) at least one surface active phospholipid selected from the group consisting of sphingolipids and phosphoglycerides,
   (b) at least one member selected from the group consisting of hyaluronic acid and its water soluble salts, and
   (c) saline solution.

* * * * *